US009895082B2

(12) United States Patent
Johnson et al.

(10) Patent No.: US 9,895,082 B2
(45) Date of Patent: Feb. 20, 2018

(54) DETECTING TEMPERATURE SENSITIVITY OF A PATIENT'S AIRWAY

(71) Applicants: Arthur T. Johnson, Darlington, MD (US); Jafar Vossoughi, Brookeville, MD (US)

(72) Inventors: Arthur T. Johnson, Darlington, MD (US); Jafar Vossoughi, Brookeville, MD (US)

( * ) Notice: Subject to any disclaimer, the term of this patent is extended or adjusted under 35 U.S.C. 154(b) by 398 days.

(21) Appl. No.: 14/815,428

(22) Filed: Jul. 31, 2015

(65) Prior Publication Data

US 2016/0038056 A1 Feb. 11, 2016

Related U.S. Application Data

(60) Provisional application No. 62/033,500, filed on Aug. 5, 2014.

(51) Int. Cl.
| | | |
|---|---|---|
| *A61B 5/085* | (2006.01) | |
| *A61B 5/087* | (2006.01) | |
| *A61B 5/097* | (2006.01) | |
| *A61B 5/08* | (2006.01) | |
| *A61B 5/091* | (2006.01) | |

(52) U.S. Cl.
CPC ............ *A61B 5/085* (2013.01); *A61B 5/087* (2013.01); *A61B 5/08* (2013.01); *A61B 5/091* (2013.01); *A61B 5/097* (2013.01)

(58) Field of Classification Search
CPC .......... A61B 5/08; A61B 5/085; A61B 5/087; A61B 5/091; A61B 5/097
See application file for complete search history.

(56) References Cited

U.S. PATENT DOCUMENTS 6,066,101 A 5/2000 Johnson et al.

OTHER PUBLICATIONS

Lausted et al., "Respiratory resistance measured by an airflow perturbation device", IOP Publishing Ltd, 1999, pp. 21-35.
Johnson et al., "Perturbation Device for Noninvasive Measurement of Airway Resistance", Medical Instrumentation 8 (2), Mar. 1974.
Johnson et al., "Validation of airflow perturbation device resistance measurements in excised sheep lungs", Institute of Physics Publishing, Physiological Measurement, May 10, 2004, pp. 679-690.

(Continued)

*Primary Examiner* — Puya Agahi
(74) *Attorney, Agent, or Firm* — Edell, Shapiro & Finnan, LLC

(57) ABSTRACT

According to one embodiment of the present invention, an airflow perturbation device for detecting airway sensitivity to temperature comprises a pneumotachometer including a flow sensor to measure airflow through the apparatus; a perturbation mechanism to periodically alter air flow resistance in the apparatus; an air cooler; a pressure sensor to measure a difference in air pressure across the pneumotachometer and perturbation mechanism; and a computing system comprising at least one processor configured to receive data from the flow sensor and pressure sensor; and determine an airflow resistance based on the received data. Embodiments of the present invention further include a method for detecting airway sensitivity to temperature in substantially the same manners described above.

16 Claims, 6 Drawing Sheets

(56) References Cited

OTHER PUBLICATIONS

Johnson et. al., "Airflow Perturbation Device for Measuring Airways Resistance of Humans and Animals", IEEE Transactions on Biomedical Engineering, vol. BME-31, No. 9, Sep. 1984, pp. 622-626.

Coursey et al., "Comparison of Expiratory Isovolume Pressure-Flow Curves With the Stop-Flow Versus the Esophageal-Balloon Method", Respiratory Care, Jul. 2011, vol. 56, No. 7, pp. 969-975.

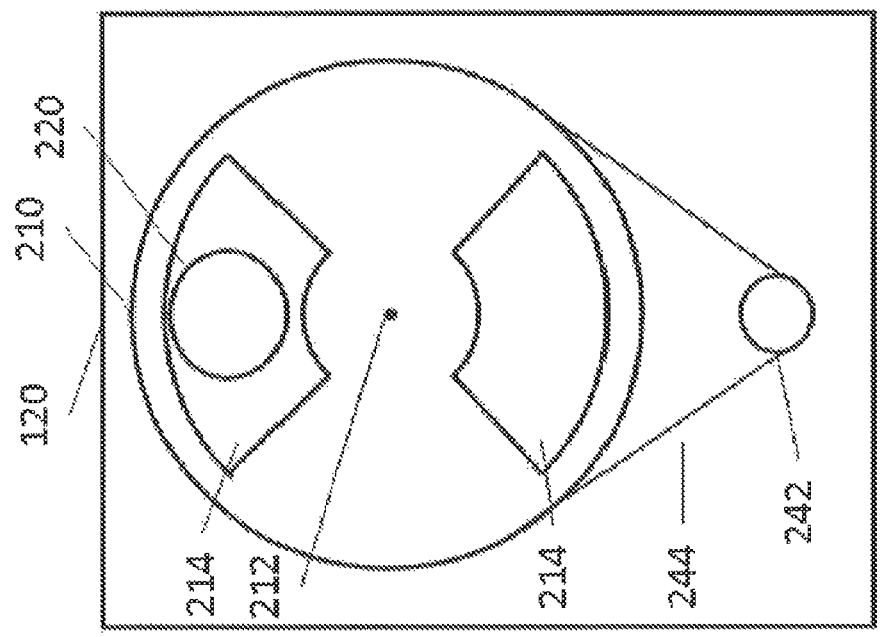
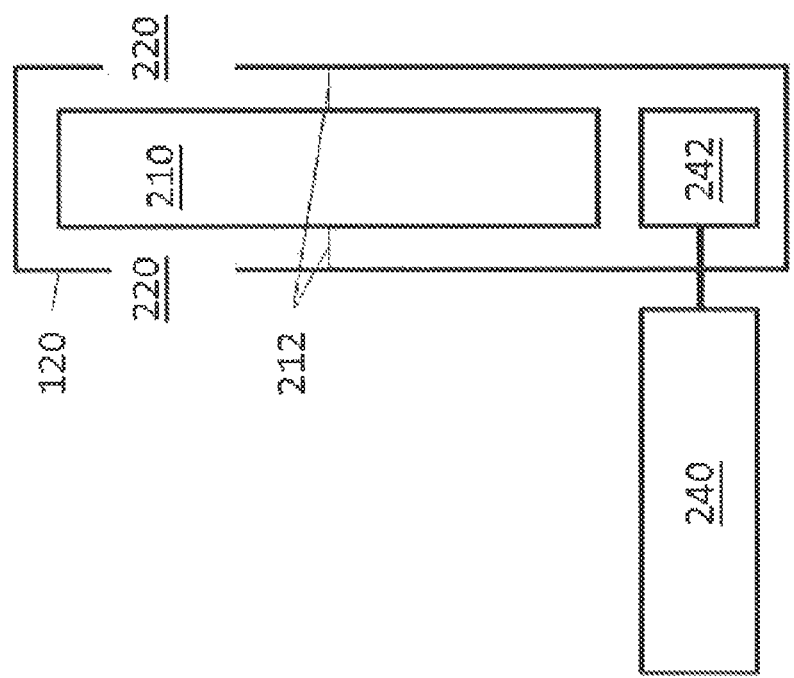

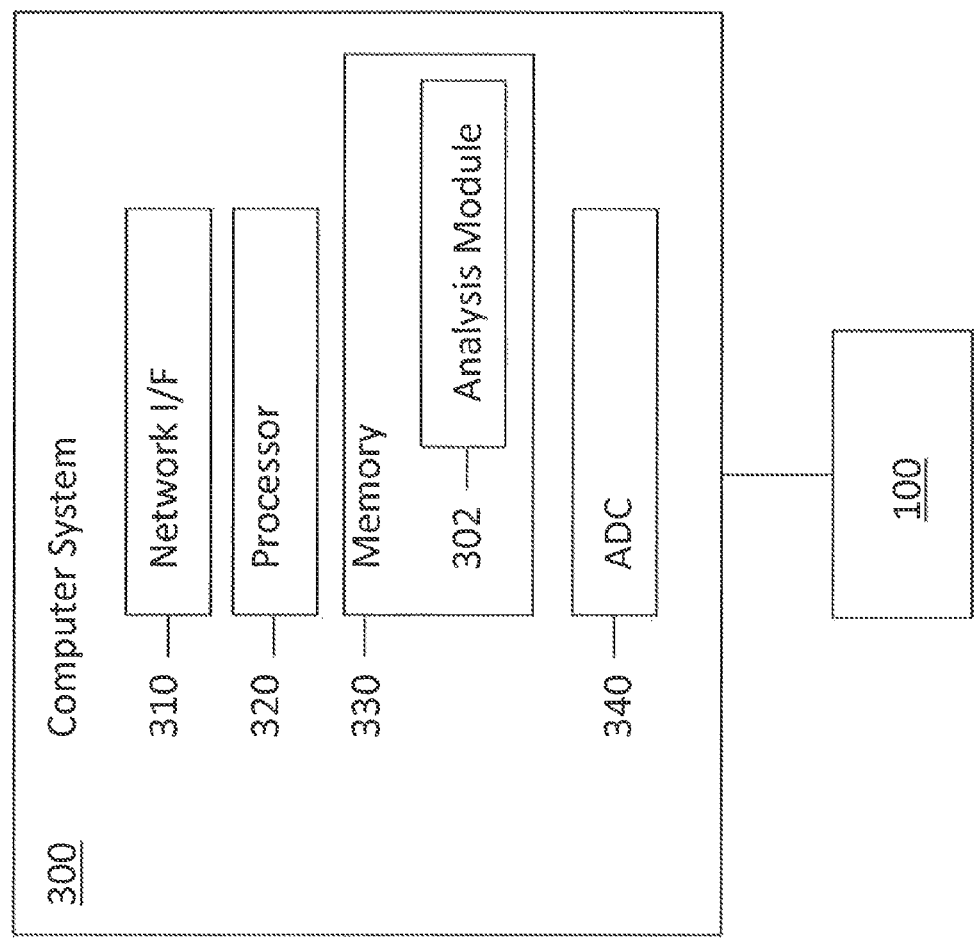

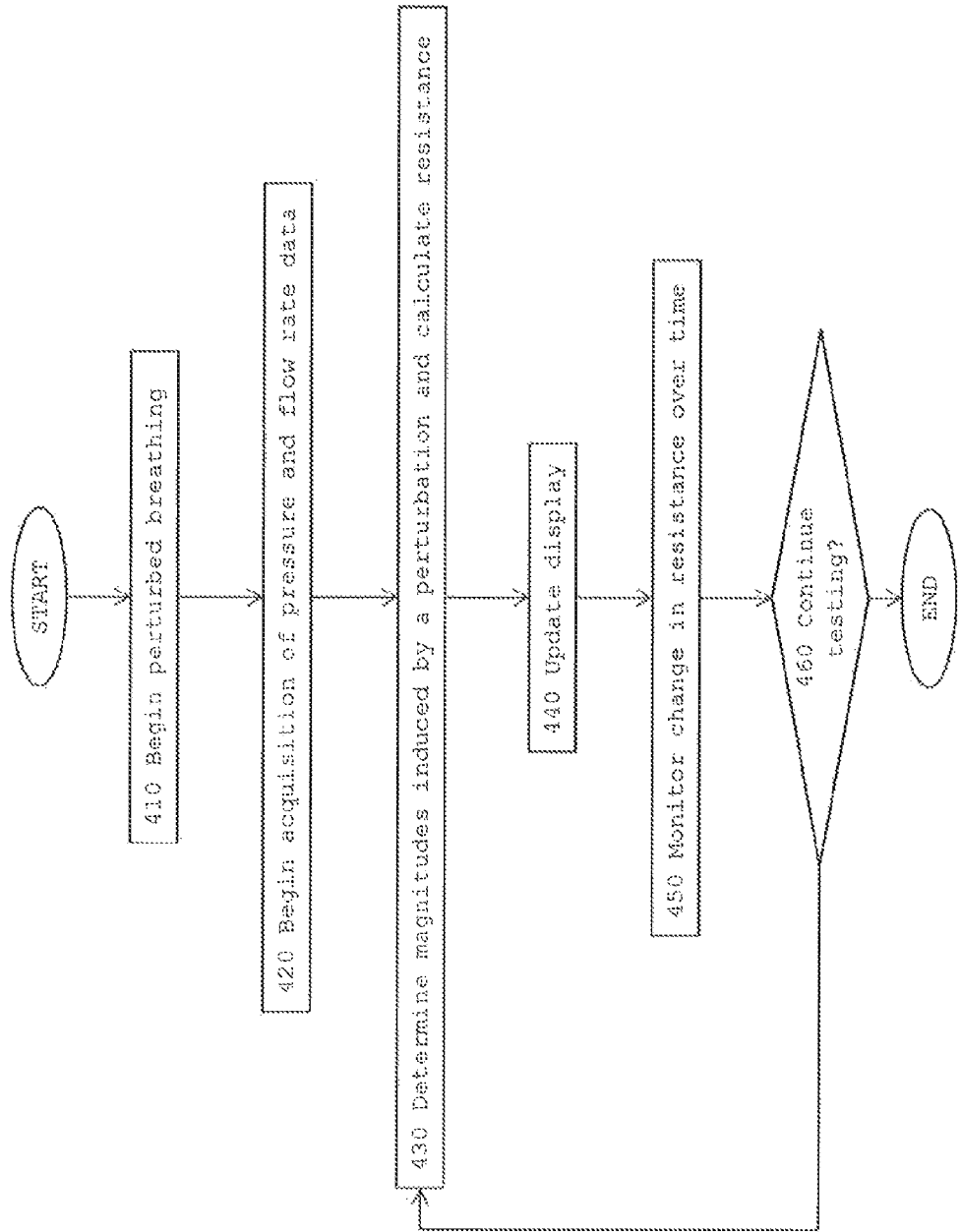

DETECTING TEMPERATURE SENSITIVITY OF A PATIENT'S AIRWAY

CROSS-REFERENCE TO RELATED APPLICATIONS

This application claims the benefit of U.S. Provisional Patent Application No. 62/033,500, titled "Detecting Temperature Sensitivity of a Patient's Airway" and filed on Aug. 5, 2014, which is incorporated herein by reference in its entirety.

BACKGROUND

Present invention embodiments relate to an airflow perturbation device and techniques for measuring parameters of respiratory mechanics, and more specifically, for detecting sensitivity of a patient's airway to temperature by measuring respiratory resistance.

The respiratory airways can develop a sensitivity to the cooling that occurs when mouth breathing during exercise. This condition is called exercise-induced asthma (EIA), exercise-induced bronchospasm, or exercise-induced bronchoconstriction. Symptoms of EIA include wheezing, tightness or pain in the chest, coughing, and in some cases, prolonged shortness of breath. Up to 80% of children with asthma have symptoms of HA when they exercise. Cold, dry air inhaled through the mouth during exercise is believed to be the main cause of these symptoms. The smooth muscle bands around the airways are sensitive to these changes in temperature and humidity and react by contracting, which narrows the airway and increases resistance to air flow. Injury to the airways from dehydration can make the smooth muscles progressively more sensitive to changes in temperature of the inhaled air.

Diagnosis of ETA is difficult, and a potential for underdiagnosis exists. In the standard diagnostic procedure, spirometry is used at rest to measure baseline pulmonary function parameters, such as Forced Expiratory Volume (FEV), Forced Expiratory Volume in One Second (FEV1), Maximum Voluntary Ventilation (MVV), Maximum Expiratory Flow Rate (MEF), and others. The patient then undergoes a treadmill or bicycle ergometer exercise session, and the spirometry testing is repeated. These procedures have several disadvantages. First, spirometry is predominantly a test of expiration and EIA symptoms are mostly felt during inhalation; second, spirometric measures only approximate respiratory resistance, which is the true symptom of interest; third, the necessity of an exercise session exposes the patient to the possibility of an unpleasant and potentially dangerous situation.

There are also pharmacological challenge tests, such as the inhalation of methacholine or mannitol used to detect airway sensitivity leading to asthma. These tests have low sensitivity for detection of EIA in athletes and are not recommended as a first-line approach in the evaluation of EIA because of the potential of these drugs to elicit extreme bronchoconstriction and dyspnea. These tests must be conducted under the supervision of a trained technician in a facility with emergency medical care available.

SUMMARY

According to one embodiment of the present invention, an airflow perturbation device for detecting airway sensitivity to temperature comprises a pneumotachometer including a flow sensor to measure airflow through the apparatus; a perturbation mechanism to periodically alter air flow resistance in the apparatus; an air cooler; a pressure sensor to measure a difference in air pressure across the pneumotachometer and perturbation mechanism; and a computing system comprising at least one processor configured to receive data from the flow sensor and pressure sensor; and determine an airflow resistance based on the received data. Embodiments of the present invention further include a method for detecting airway sensitivity to temperature in substantially the same manners described above.

BRIEF DESCRIPTION OF THE SEVERAL VIEWS OF THE DRAWINGS

Generally, like reference numerals in the various figures are utilized to designate like components.

FIGS. 2A and 2B are block diagrams of an example perturbation mechanism in cross-sectional side-view and front view respectively according to an embodiment of the present invention.

FIG. 3 is a block diagram of an example computing system for data acquisition and analysis according to an embodiment of the present invention.

FIG. 4 is a flow diagram illustrating an example manner of using an airflow perturbation device to detect airway temperature sensitivity according to an embodiment of the present invention.

DETAILED DESCRIPTION

Figure 1:
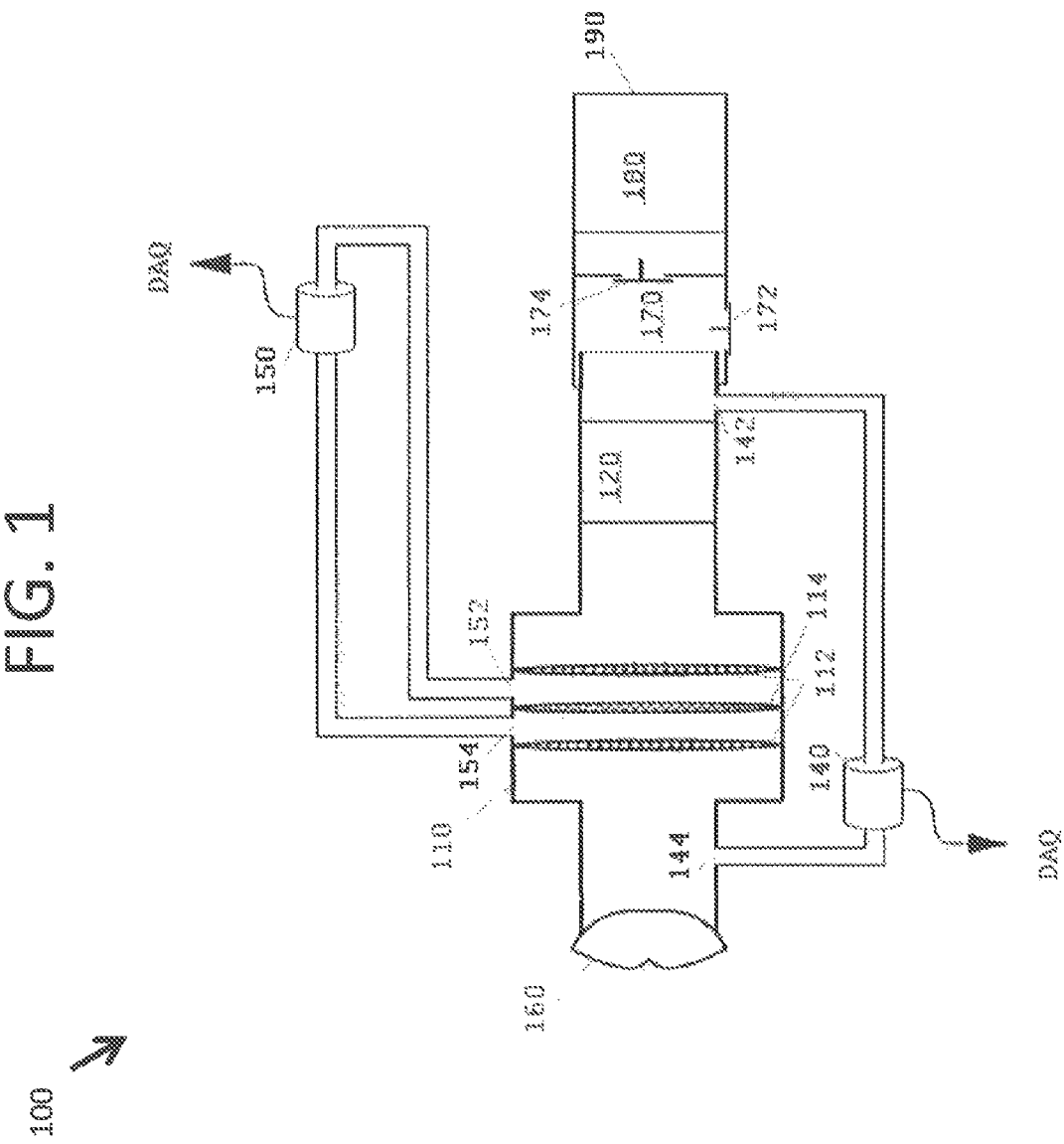
FIG. 1 is a diagrammatic illustration of an example airflow perturbation device for detecting airway temperature sensitivity according to an embodiment of the present invention.

Present invention embodiments provide an airflow perturbation device and techniques for detecting sensitivity of a patient's airway to temperature. An airflow perturbation device (APD) measures respiratory resistance internal to a patient by periodically interposing a resistance in the flow path from the patient through the APD. By way of example, this resistance may take the form of a rapidly rotating segmented wheel that intermittently creates a partial obstruction to airflow. When the resistance is in the flow pathway, the patient's breathing flow is reduced by a small amount from the flow that would have existed absent the resistance. The patient's breathing flow may be measured using a pneumotachometer. The presence of the resistance also increases the magnitude, both positive and negative, of the pressure measured at the mouth.

The measured changes in airflow and pressure at the mouth produced by the periodically interposed air flow resistance may be used to determine the patient's respiratory resistance. For example, during a time when there is no obstruction, the airflow is described by $$P_A = \dot{V}_{open} \times (R_{resp} + R_{open}) \tag{1}$$

where $$R_{open} = \frac{P_{m,open}}{\dot{V}_{open}}, \tag{2}$$

$P_A$ is respiratory pressure relative to an external location (e.g., the atmosphere or the distal side of the obstruction), $\dot{V}_{open}$ is the airflow (e.g., volume of air through the APD per time) with no obstruction, $R_{resp}$ is the respiratory resistance, $R_{open}$ is the resistance of the APD with no obstruction (e.g., the resistance of the pneumotachometer), and $P_{m,open}$ is the mouth pressure with no obstruction.

When there is a partial obstruction (e.g., from the rotating wheel), airflow is described by $$P_A = \dot{V}_{obs} \times (R_{resp} + R_{obs}) \quad (3)$$

where $$R_{obs} = \frac{P_{m,obs}}{\dot{V}_{obs}}, \quad (4)$$

$\dot{V}_{obs}$ is the air flow with a partial obstruction, $R_{obs}$ is the resistance of the flow sensor and the device with a partial obstruction, and $P_{m,obs}$ is the mouth pressure with a partial obstruction.

The equations above yield $$R_{resp} = \frac{P_{m,obs} - P_{m,open}}{\dot{V}_{open} - \dot{V}_{obs}} = \frac{\Delta P}{-\Delta \dot{V}} \quad (5)$$

The quantities $\Delta P = P_{m,obs} - P_{m,open}$ and $\Delta \dot{V} = \dot{V}_{obs} - \dot{V}_{open}$ are referred to as perturbations. They are calculated based on the peaks or valleys of the actual signals with respect to the signals that would have been present if no perturbation had occurred.

One aspect of a present invention embodiment is an airflow perturbation device useful in diagnosis of EIA by directly measuring respiratory resistance (a component of which is bronchiolar resistance) at rest while the patient inhales ambient air that has been cooled prior to inhalation through the airflow perturbation device. Such an airflow perturbation device may be referred to as an APDC. The APDC tracks respiratory resistance in real time, and changes in the resistance values are monitored. Patients with EIA will exhibit a marked positive rate of resistance increase as they breathe the cooled air. The test can be stopped by the tester at any time, thus avoiding extreme resistance increases in the patient. As patients who do not suffer EIA may show some small sensitivity to cooled air, and thus demonstrate mild respiratory resistance time rate of increase, the attending pulmonologist can use the APDC as a guide to determining if further tests are required, or if the information obtained from this test is sufficient to warrant a positive diagnosis.

Another aspect of a present invention embodiment is that testing with the APDC exposes the patient to at most only mild risk, and so can be conducted outside facilities with availability of emergency care. For example, the testing may be performed in a physician's office or local clinic.

Still another aspect of a present invention embodiment is a test for EIA that may be used with breathing through the mouth and/or breathing through the nose. For example, the APDC may typically be used with mouth breathing via a mouthpiece. Alternatively, the APDC may be used to test for nasal air temperature sensitivity by having the patient breathe into an oronasal mask with the mouth closed.

A further aspect of a present invention embodiment is a device that may be used to measure respiratory resistance and other respiratory mechanical parameters in any situation in which a resistance element (e.g., a respiratory protective device, bronchodilator administrative apparatus, etc.) is disposed directly in the breathing path.

Other aspects provided by present invention embodiments include a non-invasive, direct measurement of respiratory resistance; a lightweight, portable and inexpensive device; the capability of performing measurements in less than one minute and continuously updating those measurements; measurement of spontaneous breathing that does not require conscious or cooperative patients; separate measurement of inhalation and exhalation resistances; a device that requires no special skill to use; results that are highly reproducible with low variation; measurements that are sensitive to changes in resistance; a device that may be used to give useful resistance measurements from small children; and a device that may be used with animals.

An example airflow perturbation device with a cooling mechanism (an APDC) for detecting airway temperature sensitivity according to an embodiment of the present invention is illustrated in FIG. 1. In particular, APDC 100 comprises pneumotachometer 110, perturbation mechanism 120, pressure sensor 140, pressure taps 142 and 144, flow sensor 150, patient interface 160, valve section 170, and cooler 180.

Patient interface 160 provides an aperture via which a patient may breathe through the APDC. Example patient interfaces may include a mouthpiece, an oronasal mask, or the like.

Cooler 180 includes an aperture 190 through which ambient air may enter the cooler and be cooled. The cooler may be implemented using a commercially available or custom cooling device operating by convection cooling, thermoelectric cooling, or other heat exchange mechanism. For example, cooler 180 may be implemented using copper tubing to circulate water from an ice water batch. In one embodiment, room temperature air flowing through the cooler from aperture 190 is cooled to a temperature in the range of 32-50 degrees Fahrenheit. Alternatively, air may be cooled to temperatures above or below this range.

Valve section 170 is disposed between the cooler and the pneumotachometer/perturbation mechanism combination (the APD). The valve section includes inhalation valve 174 and exhalation valve 172. Exhalation valve 172 and inhalation valve 174 operate to reduce apparatus dead volume by directing exhaled air outside rather than back through the cooler 180. Inhalation valve 174 permits air to flow from the cooler to the APD and prevents air flow in the opposite direction. Exhalation valve 172 permits air to flow from the APD to the outside and prevents air flow into the APDC from the outside.

Pressure sensor 140 measures the pressure difference across pneumotachometer 110 and perturbation mechanism 120 via pressure taps 144 and 142. Pressure tap 144 may be disposed at or near mouthpiece 160 (e.g., between the patient interface and APD) to access the pressure at the patient's mouth. Pressure tap 142 is disposed between the APD and the cooler (e.g., between perturbation mechanism 120 and valve section 170). Signals from pressure sensor 140 and flow sensor 150 may be sent to a data acquisition system.

Pneumotachometer 110 and flow sensor 150 measure airflow between the patient and cooler through the APDC. Pneumotachometer 110 comprises airflow resistance 114 (e.g., a fine metal mesh, an array of capillaries, etc.) and may include airflow elements 112 to facilitate laminar airflow across airflow resistance 114. In one embodiment, airflow elements 112 are meshes disposed before and after airflow resistance 114. Pneumotachometer 110 further comprises pressure taps 152 and 154 disposed substantially on the cooler side and patient side, respectively, of airflow resistance 114. Flow sensor 150 may be implemented using a differential pressure sensor to measure the difference in pressure across airflow resistance 114 using pressure taps 152 and 154. This pressure difference is related to the airflow across airflow resistance 114. The pressure-airflow relationship may be modeled as a proportional or linear relationship, and may be calibrated using standard techniques.

Aspects of the device may operate in manners similar to corresponding aspects described in U.S. Pat. No. 6,066,101, which is hereby incorporated by reference in its entirety.

An example perturbation mechanism 120 is illustrated in FIGS. 2A and 2B in cross-sectional side-view and front view, respectively, according to an embodiment of the present invention. In particular, the perturbation mechanism may comprise wheel 210 disposed between opposing apertures 220. Air flowing between the patient and cooler passes into perturbation mechanism 120 through a first aperture 220, across wheel 210, and out of perturbation mechanism 120 through a second aperture 220. Wheel 210 is rotatable about shaft 212 and comprises regions of different airflow resistance such that the rotating wheel presents periodically varying resistance to the airflow between the patient and cooler. For example, wheel 120 may comprise a screen containing at least one open region 214 having a size and location to substantially cover apertures 220 during a portion of the wheel's rotation. Alternatively, region 214 may be screened and the remainder of the wheel may be substantially open or have a screen of another gauge than region 214 to provide a different airflow resistance. Alternatively, the wheel may comprise one or more solid regions that block the airflow.

Rotation of wheel 210 may be driven by motor 240, using pulley 242, and drive belt 244. Motor 240 may be contained within the sealed APDC housing. Power for the motor may be supplied by batteries residing within the housing. Alternatively, the APDC housing may be sealed around a passthrough for a power chord to provide power from an external source.

In alternative embodiments, perturbations to the airflow may be produced in a manner other than with a wheel (for instance, by pinching a tube or using a shutter). In an embodiment using a pinching mechanism, the mechanism may be configured to pinch a tube at most partly closed in order ensure a pathway in the event mechanism fails. A pinching mechanism may be implemented using an electrical function generator and electro-sensitive materials that contract as the voltage increases, or in any other electrical or mechanical manner. In an embodiment using a shutter mechanism, the shutters may be implemented using screens to avoid complete blockage of the airflow. In any embodiment, the perturbation mechanism may include a plurality (e.g., two, three, etc.) of pathways (e.g., tubes), of which fewer than all are perturbed (e.g., pinched or obstructed by a shutter or wheel).

An example computing system for data acquisition and analysis according to an embodiment of the present invention is illustrated in FIG. 3. In particular, computing system 300 may be implemented by a conventional or other computer system preferably equipped with a display or monitor, a base (e.g., including at least one processor 320, memories 330, analog-to-digital converter (ADC) 340, and/or other external or internal network interface or communications devices 310 (e.g., modem, network cards, etc.)), optional input devices (e.g., a keyboard, mouse, or other input device), and any commercially available and custom software (e.g., analysis module 302 software, ADPV driver software, database software etc.)).

Analysis module 302 may include one or more modules or units (e.g., ApplyCalibration module, FindPerturbations module, GetVirtualData module, CalcResistance module, Display module, etc.) to perform the various functions of present invention embodiments described below (e.g., calibrating transducer signals, detecting begin and end points of perturbations, interpolating between perturbation begin and end points, calculating respiratory resistance, etc.), may be implemented by any combination of any quantity of software and/or hardware modules or units, and may reside within memory 330 of computing system 300 for execution by processor 320. The analysis module may be implemented across plural computing systems. The computing system(s) may present any graphical user (e.g., GUI, etc.) or other interface (e.g., command line prompts, menu screens, etc.) to receive commands from users and interact with the analysis module, APDC, and/or other modules, devices, or services.

Computing system 300 communicates with APDC 100 to receive signals from pressure sensor 140 and flow sensor 150, and may communicate with other systems (e.g., database systems, client systems, server systems, etc.) over a network implemented by any number of any suitable communications media (e.g., wide area network (WAN), local area network (LAN), Internet, intranet, etc.). Computing system 300 may utilize any local or remote data sources implemented by any conventional information storage system (e.g., relational database, file system server, etc.).

Figure 5B:
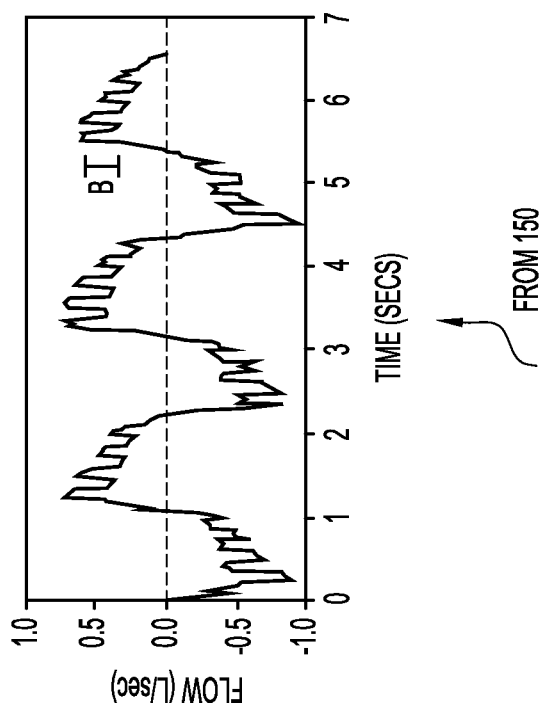
FIGS. 5A and 5B are illustrations of example mouth pressure and flow signals respectively according to an embodiment of the present invention.
Figure 5A:
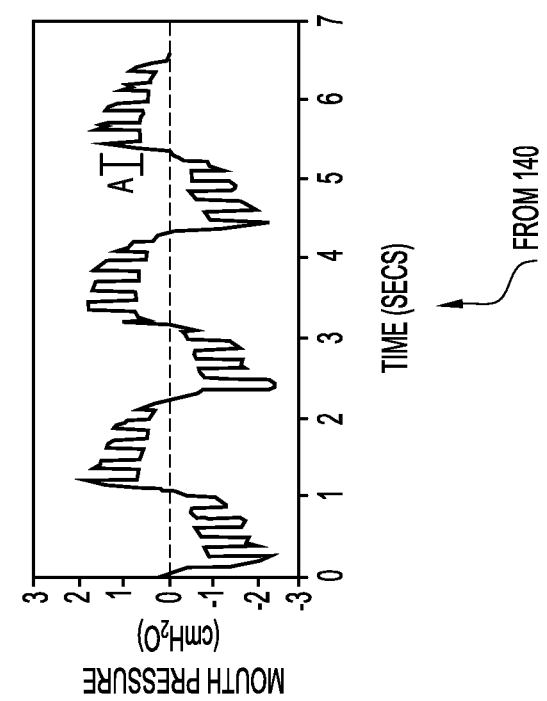
Figure 6:
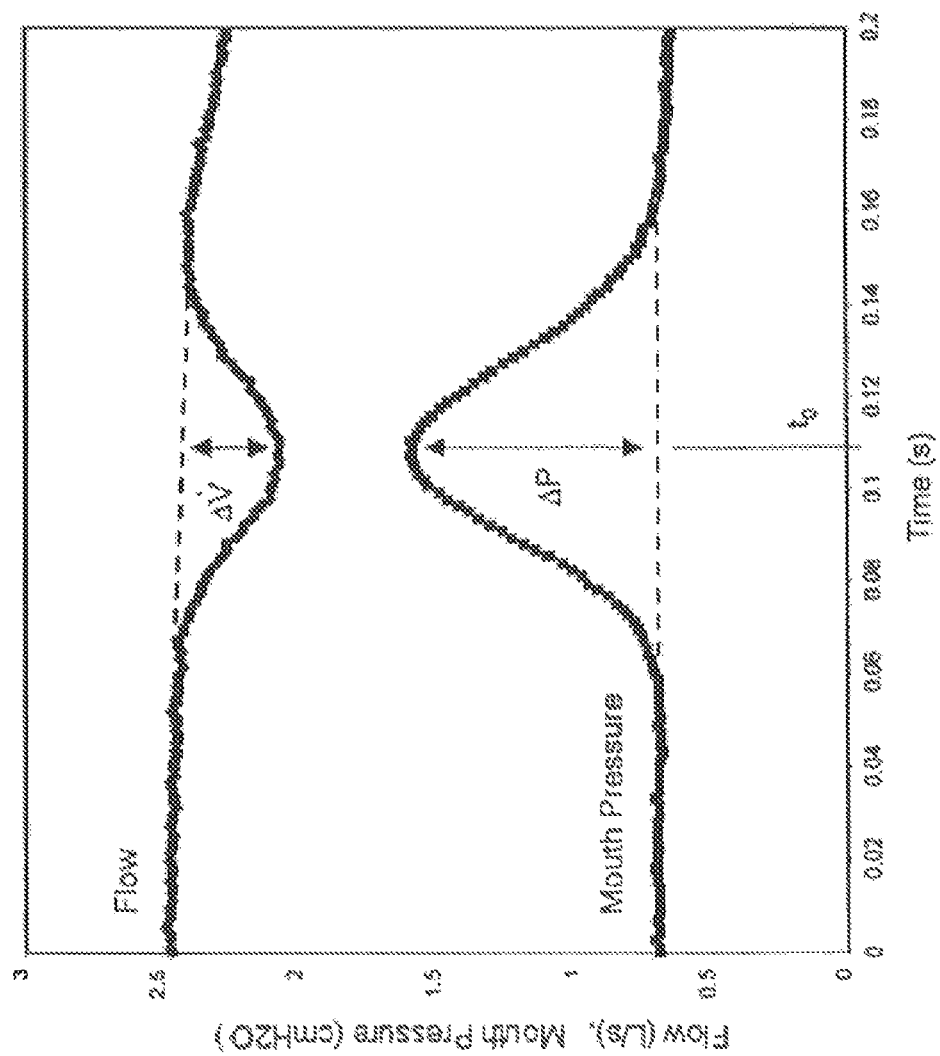
FIG. 6 is an illustration of example pressure and flow signals for an individual perturbation according to an embodiment of the present invention.

An example manner of determining airflow resistance of a patient to detect airway temperature sensitivity according to an embodiment of the present invention is illustrated in FIGS. 4-6. Testing is initiated at step 410. If the cooler is implemented as an active device, the cooler is turned on. The perturbation mechanism is activated, e.g., by engaging power to motor 240. The patient breathes cooled air through the APDC.

At step 420, acquisition of pressure and flow rate data begins. The pressure transducers of pressure sensor 140 and flow sensor 150 send electric signals to computer system 300. ADC 340 digitizes the signals. Analysis module 302 continually monitors and records the digitized signals from the pressure transducers for mouth pressure and pneumotachometer flow sensor. The analysis module may apply predetermined calibrations to the data (e.g., converting digitized pressure transducer data from pressure sensor 140 to units of pressure, converting digitized pressure transducer data from flow sensor 150 to units of volume per time based on a measured resistance of airflow resistance 114, etc.). Example data from pressure sensor 140 and flow sensor over time are illustrated in FIGS. 5A and 5B, respectively. The larger period structure corresponds to the patient's breathing. The perturbation mechanism induces the smaller time-scale structure; the resulting changes in the mouth pressure may have a typical magnitude indicated by A, and the changes in the air flow may have a typical magnitude indicated by B.

At step 430, analysis module 302 determines the pressure and flow changes due to an individual perturbation and performs a calculation of the respiratory resistance based on those changes. Typically, the analysis module operates in real-time. Example mouth pressure and air flow data for an individual perturbation are illustrated in FIG. 6. The analysis module interpolates (e.g., linearly) the mouth pressure and flow rate data between the points when the signals are essentially unperturbed (e.g., when the wheel resistance is zero) immediately preceding the perturbation and immediately following the perturbation. These interpolated signals are referred to as virtual signals and are indicated by the dashed lines in FIG. 6. Changes in mouth pressure and flow rate induced by the perturbation mechanism are measured with respect to the corresponding virtual signals. In particular, the changes may be computed as the observed signal minus the virtual signal. The analysis module determines the time ($t_0$) at which the magnitudes of the changes are greatest. The pressure change ($\Delta P$) and flow change ($\Delta \dot{V}$) at $t_0$ may be used to calculate respiratory resistance using Eq. 5. These data may be separated, based on flow signal polarity, into resistance during inspiration and resistance during expiration. This separation can be useful for determining abnormalities that affect one or another of the breathing phases.

At step 440, the analysis module may update the display to indicate the calculated respiratory resistance. For example, the display may show the most recent respiratory resistance calculation, a list of the most recent respiratory resistance calculations, a graph of the most recent respiratory calculations versus time, or the like. Respiratory resistance is normally calculated once for each perturbation.

At step 450, the change in respiratory resistance over time is monitored in real time. Patients with EIA will exhibit a marked positive rate of increase in resistance as they breathe the cooled air. If a patient's respiratory resistance increases by more than a predetermined threshold since the first measurement after step 420, then EIA may be indicated. For example, if the patient's airway resistance increases by a factor in the range of 2-3, a positive result may be indicated. If a patient's respiratory resistance increases by more than another, lower, predetermined threshold since the first measurement after step 420, then possible EIA and other testing may be indicated.

At step 460, a determination is made as to whether to continue testing the patient. If the determination is to continue testing, processing returns to step 430, and the next perturbation is detected and analyzed. The test may be stopped by the tester at any time, thus avoiding extreme resistance increases in the patient's airway resistance (e.g., a factor of five increase). For example, the test may be stopped if the patient's airway resistance increases by a factor of 2 or 3. Otherwise, the test may be stopped after a predefined interval (e.g., one minute, two minutes, etc.).

It will be appreciated that the embodiments described above and illustrated in the drawings represent only a few of the many ways of implementing embodiments for detecting airway sensitivity of patients.

Present invention embodiments may be used to measure respiratory resistance and other respiratory mechanical parameters in any situation in which a resistance element is disposed directly in the breathing path. Examples of such resistance elements include cooler 180, respiratory protective devices, a bronchodilator administrative apparatus, and the like. In each such case, the resistive element or elements may take the place of cooler 180 in FIG. 1. For example, workers required to wear respiratory protective equipment must undergo an annual assessment of their ability to wear respirator masks. At present, there is no satisfactory means to determine quantitatively if the masks represent a burden too great for the wearer. The APDC may provide the means to perform this test in the workplace.

In the case of a bronchodilator apparatus, a bronchodilator drug is usually administered through an aerosolizer from which the patient inhales. The bronchodilator drug dose is administered based at least partially upon the weight of the patient. This gives only an approximate dose to dilate the airways. It is possible that a dose larger than the amount necessary to reduce respiratory resistance to the target value is given to the patient. This is because no direct measure of the resistance is made while the drug is being given. Common bronchodilator drugs are beta blockers that can raise heart rate as a side effect, which can be an unpleasant sensation. The APDC can be used between the patient and the aerosolizer to monitor resistance in real time. When the target resistance value has been reached, the respiratory therapist can cease administering the drug. If the dead volume of the aerosolizer and the APDC combination is not too large, then the directional valves 172 and 174 may be omitted.

An embodiment of the present invention may utilize any conventional or other pneumotachometer technology, pressure sensors, and perturbation mechanism (e.g., rotary wheel, shutter, pinch techniques, etc.). Any type of cooling or heating mechanism may be used.

The environment of the present invention embodiments may include any number of computer or other processing systems (e.g., client or end-user systems, server systems, etc.) and storage systems (e.g., file systems, databases, or other repositories), arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., database software, communications software, etc.). These systems may include any types of monitors and input devices (e.g., keyboard, mouse, voice recognition, touch screen, etc.) to enter and/or view information.

It is to be understood that the software of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

What is claimed is:

1. A system for measuring respiratory resistance comprising:
   an element providing airflow resistance in an airflow pathway, wherein the element comprises a cooler and the cooler comprises an aperture for receiving ambient air into the cooler;
   an airflow perturbation device comprising:
   a pneumotachometer including a flow sensor to measure airflow in the pathway; and
   a perturbation mechanism to periodically alter air flow resistance in the pathway;
   a first pressure tap disposed to access pressure in the pathway between an inlet and the airflow perturbation device;
   a second pressure tap disposed to access pressure in the pathway between the element and the airflow perturbation device; and
   a pressure sensor to measure a difference in air pressure across the pneumotachometer and perturbation mechanism using the first and second pressure taps.

2. The system of claim 1, further comprising:
   a computing system comprising at least one processor configured to:
   receive data from the flow sensor and pressure sensor; and
   determine a respiratory resistance based on the received data.

3. The system of claim 2, wherein the at least one processor is further configured to display the determined respiratory resistance.

4. The system of claim 1, further comprising a first valve to direct air from the airflow perturbation device out of the pathway and a second valve to direct air from the airflow resistance element to the airflow perturbation device.

5. The system of claim 1, wherein the cooler is configured to cool entering air to a temperature in the range of 32 to 50 degrees Fahrenheit.

6. The system of claim 2, wherein the at least one processor is further configured to track the respiratory resistance over time based on the received data.

7. The system of claim 1, wherein the perturbation mechanism comprises a selected one of a mechanism for pinching a flexible tube, a rotating segmented wheel, and a shutter.

8. The system of claim 2, wherein determining the respiratory resistance comprises determining changes in pressure and airflow with respect to corresponding pressure and airflow expected in the absence of the alteration to the air flow resistance.

9. The system of claim 8, wherein the changes in the pressure and airflow expected in the absence of the alteration are determined by interpolating signals between perturbations.

10. A method of measuring respiratory resistance based on flowing air in a pathway having an airflow resistance element, the method comprising:
    periodically perturbing airflow resistance in the pathway using an airflow perturbation mechanism;
    measuring airflow through the pathway using a pneumotachometer having a flow sensor;
    measuring a difference in air pressure across a system formed of the perturbation mechanism and pneumotachometer using a pressure sensor and first and second pressure taps, wherein the airflow resistance element comprises a cooler and the cooler comprises an aperture for receiving ambient air into the cooler, wherein the first pressure tap is disposed to access pressure in the pathway between an inlet and the system, and wherein the second pressure tap is disposed to access pressure in the pathway between the airflow resistance element and the system;
    receiving data from the flow sensor and pressure sensor at a computing system comprising at least one processor; and
    determining, via the at least one processor, a respiratory resistance based on the received data.

11. The method of claim 10, further comprising cooling air for the subject to inhale to a temperature in the range of 32 to 50 degrees Fahrenheit using the cooler.

12. The method of claim 10, further comprising:
    tracking the respiratory resistance in real time.

13. The method of claim 12, further comprising:
    indicating a sensitivity of a subject's respiratory airway to cooling in response to an increase of the determined respiratory/airflow resistance by a threshold amount.

14. The method of claim 12, further comprising:
    indicating a sensitivity of a subject's respiratory airway to cooling in response to an increase of the determined respiratory/airflow resistance by a factor in the range of two to three.

15. The method of claim 12, further comprising:
halting delivery of cooled air in response to an increase of the determined respiratory/airflow resistance by a factor in the range of two to three.

16. The method of claim 12, further comprising:
halting delivery of cooled air in response to an increase of the determined respiratory/airflow resistance by a predetermined factor greater than three.

* * * * *